United States Patent
Caterini et al.

(10) Patent No.: US 6,610,015 B2
(45) Date of Patent: Aug. 26, 2003

(54) DEVICE AND METHOD FOR MEASURING THE CHANGE IN DIAMETER OF A VEIN BY THE DOPPLER EFFECT

(75) Inventors: Richard Caterini, Orlienas (FR); Michel Trifot, Genas (FR)

(73) Assignee: Delegation Generale pour l'Armement DSP/SREA/BPI, Arcueil (FR)

(*) Notice: Subject to any disclaimer, the term of this patent is extended or adjusted under 35 U.S.C. 154(b) by 53 days.

(21) Appl. No.: 09/920,741

(22) Filed: Aug. 3, 2001

(65) Prior Publication Data

US 2002/0043619 A1 Apr. 18, 2002

(30) Foreign Application Priority Data

Aug. 3, 2000 (FR) .......................... 00 10238

(51) Int. Cl.[7] ................................ A61B 8/06
(52) U.S. Cl. .................................... 600/453
(58) Field of Search ................ 600/437, 453–456, 600/459, 461, 480–484, 300

(56) References Cited

U.S. PATENT DOCUMENTS

| | | | |
|---|---|---|---|
| 3,810,459 A | 5/1974 | Becker | |
| 4,667,679 A | * 5/1987 | Sahota | 600/454 |
| 5,259,386 A | * 11/1993 | Sharkawy | 600/461 |
| 5,309,915 A | * 5/1994 | Ember | 600/453 |
| 5,309,916 A | 5/1994 | Hatschek | |
| 5,313,947 A | 5/1994 | Micco | |
| 5,522,878 A | 6/1996 | Montecalvo et al. | |
| 5,843,007 A | * 12/1998 | McEwen et al. | 601/152 |
| 6,017,307 A | * 1/2000 | Raines | 600/300 |
| 6,132,379 A | * 10/2000 | Patacsil et al. | 600/459 |

* cited by examiner

*Primary Examiner*—Francis J. Jaworski
(74) *Attorney, Agent, or Firm*—Oliff & Berridge, PLC

(57) ABSTRACT

The invention relates to a device for measuring the change in the diameter of a vein by the Doppler effect. The device operates such that when a first signal is generated, it controls a transmission and reception probe in continuous mode in order to obtain an audible signal from a speaker as a function of the position of a transmission and reception probe relative to a vein in order to locate the vein, and when a second signal is generated once the vein has been located, the second signal controls the transmission and reception probe in discontinuous mode and, from the changes in frequency between the transmitted and received ultrasonic waves, determines the diameter of the vein to ensure that its changes are displayed.

20 Claims, 2 Drawing Sheets

DEVICE AND METHOD FOR MEASURING THE CHANGE IN DIAMETER OF A VEIN BY THE DOPPLER EFFECT

BACKGROUND OF THE INVENTION

The invention relates to the technical field of measuring the diameter of a vein of a patient by the Doppler effect.

The subject of the invention is applied particularly advantageously in the area of monitoring the blood volume of a patient.

In the above technical area, it should be borne in mind that management of hypovolemic shock involves rapid volume replacement. Hence physicians tend to infuse the patient rapidly with replacement fluids. Fluid overload frequently occurs, diluting the coagulation factors and thus increasing the risk of bleeding and tissue infiltration to create, for example, cerebral and pulmonary edema.

Hence there is a need to monitor changes in blood volume during this delicate therapeutic phase, essential for the patient.

SUMMARY OF THE INVENTION

Since blood volume is not currently measured in an effective manner, the idea emerged of evaluating the change in cross section of certain veins able to expand, such as the jugular or femoral vein, during volume replacement. Observing the change in diameter of a vein enables the level of vascular filling to be monitored and hence the filling rate to be determined.

Hence a device is needed to determine the change in diameter of an expanding vein to evaluate the blood volume replacement rate of a patient who may be under adverse environmental conditions, such a device being designed to be autonomous, small in size, and very easy to use.

The goal of the invention is thus to meet this need by offering a device for measuring the change in diameter of a vein by the Doppler effect.

According to the invention, the device has, in a housing:
- at least one ultrasonic wave transmission and reception probe connected to a control and processing unit,
- processing means as part of the control and processing unit that are designed to determine the difference in frequency between the transmitted and received ultrasonic waves,
- a speaker connected to the output of the processing means,
- a display means connected to the control and processing unit designed to display the change in diameter of the vein,
- a means for generating a first signal triggering an operating phase of the transmission and reception probe in continuous mode,
- a means for generating a second signal triggering an operating phase of the transmission and reception probe in discontinuous mode,
- and a control and processing unit designed:
- when generating the first signal, to control the transmission and reception probe in continuous mode in order to obtain an audible signal from the speaker as a function of the position of the transmission and reception probe relative to the vein in order to locate the vein, and
- when the second signal is generated once the vein has been located, to control the transmission and reception probe in discontinuous mode and, from the changes in frequency between the transmitted and received ultrasonic waves, determine the diameter of the vein to ensure that its changes are displayed, and
- an electrical power supply for the various electrical components of the device.

The subject of the invention is also directed at offering a novel method for measuring the change in diameter of a vein by the Doppler effect. According to the invention, the method consists of:
- applying the transmission and reception probe of the device to the skin of the patient,
- controlling the operation of the transmission and reception probe in continuous mode,
- moving the transmission and reception probe on the skin of the patient until an audible signal is obtained corresponding to the location of the vein sought,
- holding the transmission and reception probe in a fixed position,
- controlling the operation of the transmission and reception probe in discontinuous mode in order to determine the diameter of the vein from the differences in frequency between the transmitted and received ultrasonic waves,
- and displaying the changes in diameter of the vein.

BRIEF DESCRIPTION OF THE DRAWINGS

Various other features will emerge from the description provided below with reference to the attached drawings which show, as nonlimiting examples, exemplary embodiments of the subject of the invention.

DETAILED DESCRIPTION OF PREFERRED EMBODIMENTS

Figure 1:
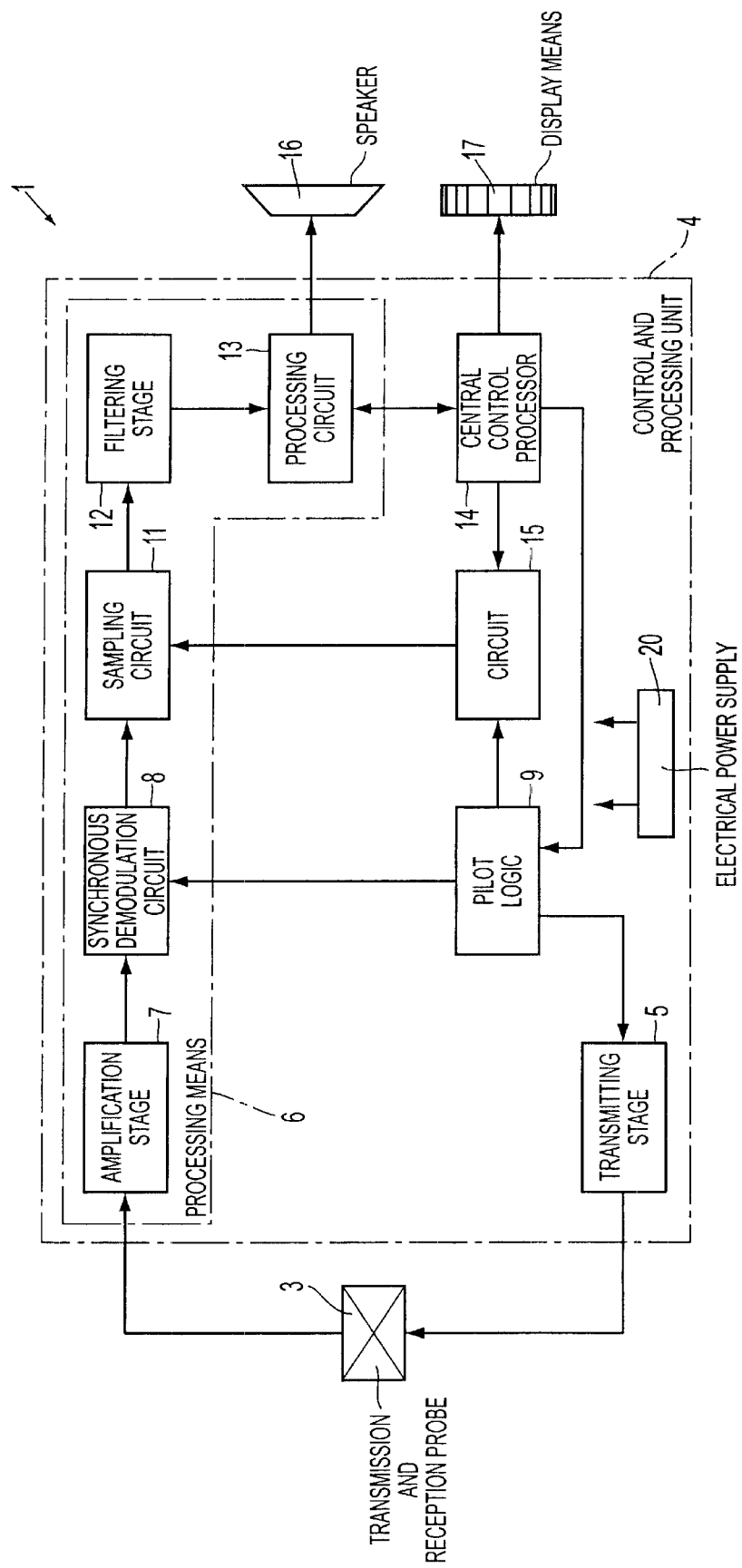
FIG. 1 is a functional block diagram of the measuring device according to the invention.
Figure 2:
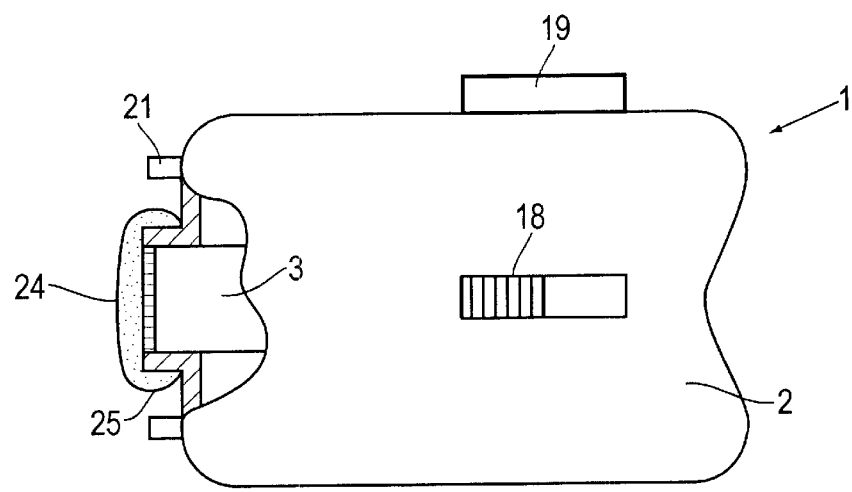
FIG. 2 is a partial schematic view of one exemplary embodiment of the device according to the invention.
Figure 3:
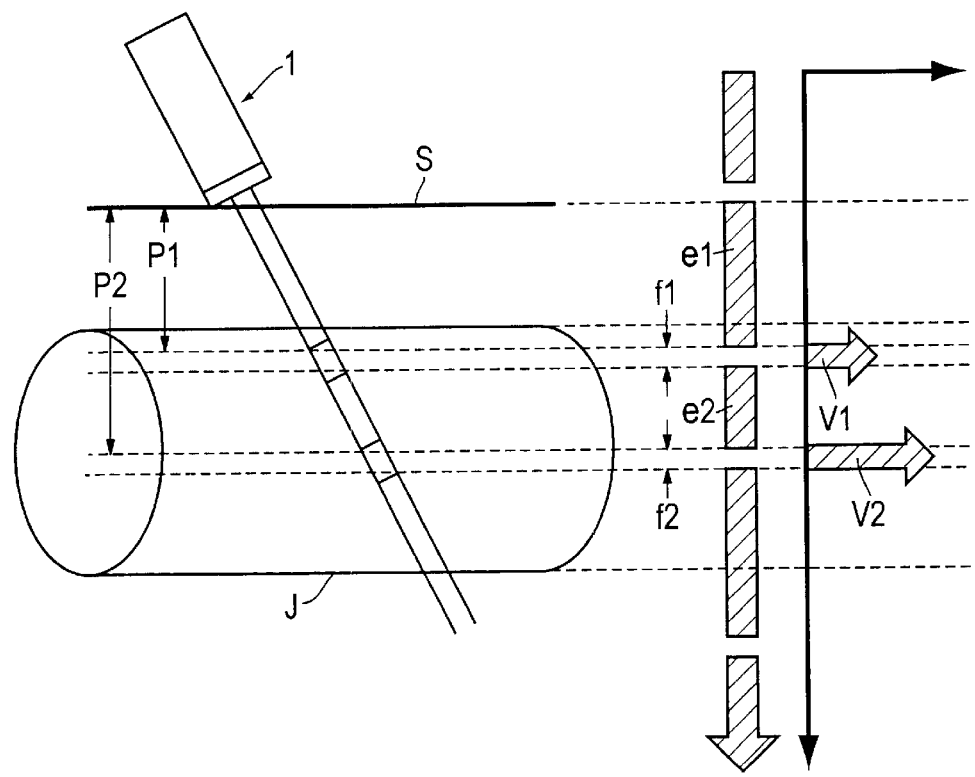
FIG. 3 is a schematic diagram illustrating one advantageous feature of the subject of the invention.

As can be seen more precisely in FIGS. 1 to 3, the subject of the invention is a device 1 designed to measure the change in diameter of a vein J shown in FIG. 3, by the Doppler effect. Device 1 according to the invention is in the form of a small housing 2 which can be manipulated to position it on the skin S of a patient below which is located a vein J with the ability to expand, such as the femoral vein or jugular vein.

Device 1 has an ultrasonic wave transmission and reception probe 3 connected to a control and processing unit 4. More specifically, control and processing unit 4 has a transmitting stage 5 delivering a sine-wave electrical signal to transmission and reception probe 3 in order to ensure transmission of ultrasonic waves. For example, transmission and reception probe 3 has a transmitting ceramic component that, by the piezoelectric effect, converts the electrical signal received from transmitting stage 5 into a mechanical phenomenon with the same frequency. This transmitting ceramic component thus produces a high-frequency mechanical vibration causing generation of an ultrasonic wave that propagates in a privileged direction perpendicular to the surface of the transmitting ceramic component. Such an ultrasonic beam propagates in the tissues until it encounters vein J in which the formed elements of the blood act as reflectors. The reflected waves are thus received by transmission and reception probe 3 which also has a receiving ceramic component that, by the inverse piezoelectric effect, converts the received ultrasonic waves into an electrical signal with the same frequency.

Control and processing unit 4 has processing means 6 designed to determine the difference in frequency between the transmitted ultrasonic waves and the received ultrasonic waves. Processing means 6 comprises a stage 7 in which the signals received by transmission and reception probe 3 are amplified. The output of amplification stage 7 is connected to a synchronous demodulation circuit 8 driven by a pilot logic 9 that controls transmitting stage 5. The output of demodulation circuit 8 is connected through a sampling circuit 11 to a filtering stage 12. The output of filtering stage 12 is connected to a processing circuit 13 designed to determine the difference in frequency between the transmitted and received signals. Processing circuit 13 is connected to a central control microprocessor 14 that also controls pilot logic 9 and a circuit 15 that generates a measuring window, the function of which will be described more precisely below.

Device 1 according to the invention also has a speaker 16 connected to the output of processing means 6 and a display means 17 connected to microprocessor 14 and designed to display, for example, the change in diameter of vein J.

Measuring device 1 according to the invention also has a means 18 for generating a first signal that triggers an operating phase of transmission and reception probe 3 in continuous mode. Such a generating means 18 is comprised for example by a switch that turns on device 1.

Device 1 according to the invention also has a means 19 generating a second signal that triggers an operating phase of transmission and reception probe 3 in discontinuous mode. For example, the second-signal-generating means 19 can be a pushbutton easily accessible to the user. Measuring device 1 according to the invention also has an electrical power supply 20 for the various electrical or electronic components mounted inside housing 2. Control and processing unit 4 also has programming means for implementing the measuring method as described below.

When the first signal is generated by on-switch 18, the control and processing unit 4 controls the transmission and reception probe 3 in continuous mode. In other words, the transmission and reception probe continuously transmits ultrasonic waves with a frequency of between 3 and 7 MHz, preferably approximately 4 MHz. Device 1 is positioned on skin S of the patient in order to locate the desired vein J. Processing means 6 determine the difference in frequency between the transmitted ultrasonic waves and the received ultrasonic waves. The difference in frequency is transmitted to speaker 16 which furnishes an audible signal for locating vein J. Indeed, it must be considered that the signal furnished by speaker 16 enables the arterial flow, which is noisy and high in frequency because it is fast and powerful, to be distinguished from the blood flowing in a vein, characterized by a dull, less powerful sound. Device 1 is thus moved until the sound obtained from speaker 16 is characteristic of the presence of a vein J. The audible signal delivered by speaker 16 thus serves for orientation and positioning of device 1 relative to the target vein J.

Once vein J is located, the device 1 is held in position on the skin of the patient. It should be noted that device 1 can have a marking system 21 mounted at a given distance from the transmission and reception probe 3 for locating the transmission and reception probe 3 corresponding to the location of vein J, on the skin S of the patient. For example, such a marking system 21 can be a writing system that marks for example two points on the skin half-way between which the transmission and reception probe 3 is located.

Once vein J has been located, the user, using second-signal-generating means 19, triggers a second operating phase of transmission and reception probe 3 in discontinuous mode. In this phase, the control and processing unit 4 enables the diameter of the vein to be determined from the differences in frequency between the transmitted and received ultrasonic waves so that the changes can be displayed. The transmission and reception probe 3 thus transmits the ultrasonic waves discontinuously with a frequency of between 3 and 7 MHz, preferably approximately 4 MHz.

For this purpose, the control and processing unit 4 drives the transmission and reception probe 3 to ensure successive transmission of ultrasonic wave pulses $e_1, e_2, e_3. \ldots, e_i$ each separated by a measuring window $f_1, f_2, f_3, \ldots, f_i$ of the ultrasonic waves received. During the time interval separating two successive pulse transmissions $e_i$, the flow rate $V_1$ is determined. As shown in the example illustrated in FIG. 3, once each pulse $e_1, e_2$ has been transmitted, i.e. during measuring windows $f_1, f_2$, respectively, a velocity $V_1, V_2$ respectively is determined corresponding to the reflecting elements contained in vein J and located at level $P_1, P_2$ respectively relative to skin S of the patient.

According to one preferred embodiment, the transmission frequency of the ultrasonic wave pulses $e_i$ is variable to ensure complete scanning of a section of vein J. For this purpose, microprocessor 14 controls the circuit 15 generating a measuring window $f_1$, in order to ensure the time difference between the measuring windows that occurs between each variable-frequency pulse. Thus, the velocity curve V can be determined over a given section of vein J enabling the walls of the vein to be pinpointed. In this way, the blood flow rate curve over a section of vein can be determined. The actual diameter of vein J can be determined from the position of device 1 relative to the axis of vein J. The diameter values of vein J are thus displayed on display means 17 for evaluating the change in diameter of vein J. For example, display means 17 can be a bar graph.

According to one preferred embodiment, device 1 has an acoustic matching membrane 24, the impedance of which is matched to the ultrasonic waves to favor acoustic matching between the ultrasonic transduction electronics and the skin of the patient. The acoustic matching membrane 24 is mounted opposite transmission and reception probe 3. The acoustic matching membrane 24 has mounting means movable on the housing so that they can be removed after use. For this purpose, the acoustic matching membrane 24 can be made in the form of a cap that fits into an annular groove 25 provided on housing 2 such that the cap is opposite transmission and reception probe 3. Such a membrane, which can be made of silicone or a thin felt pad soaked in acoustic gel injected under pressure, has the feature of attenuating the ultrasonic waves only very slightly. During the storage phase, such a membrane can be covered with a protective film that can be removed before being mounted on housing 2.

What is claimed is:

1. A device for measuring the change in diameter of a vein by the Doppler effect, comprising:
   a housing;
   at least one ultrasonic wave transmission and reception probe connected to a control and processing unit in the housing;

processing means as part of the control and processing unit that are designed to determine the difference in frequency between the transmitted and received ultrasonic waves;

a speaker connected to the output of the processing means;

a display means connected to the control and processing unit designed to display the change in diameter of the vein;

a means for generating a first signal triggering an operating phase of the transmission and reception probe in a continuous mode;

a means for generating a second signal triggering an operating phase of the transmission and reception probe in a discontinuous mode;

a control and processing unit that, when generating the first signal, controls the transmission and reception probe in continuous mode in order to obtain an audible signal from the speaker as a function of the position of the transmission and reception probe relative to the vein in order to locate the vein, and that, when the second signal is generated once the vein has been located, controls the transmission and reception probe in discontinuous mode and, from the changes in frequency between the transmitted and received ultrasonic waves, determines the diameter of the vein to ensure that its changes are displayed; and an electrical power supply for the various electrical components of the device.

2. The device according to claim 1, wherein the control and processing unit in discontinuous mode drives the transmission and reception probe to ensure successive transmission of ultrasonic wave pulses, each wave pulse separated by a window measuring the received ultrasonic waves to determine the change in frequency, with the pulse transmission frequency being variable to ensure that the vein pattern is scanned.

3. The device according to claim 2, wherein the device further comprises an acoustic matching membrane mounted opposite the transmission and reception probe.

4. The device according to claim 3, wherein the device further comprises a marking system mounted at a specific distance from the transmission and reception probe to position the transmission and reception probe at exact locations on the skin of a patient.

5. The device according to claim 1, wherein the control and processing unit drives the transmission and reception probe in continuous mode to ensure transmission of ultrasonic waves with a frequency of between 3 and 7 MHz.

6. The device according to claim 1, wherein the control and processing unit drives the transmission and reception probe in discontinuous mode to ensure transmission of ultrasonic waves with a frequency between 3 and 7 MHz.

7. The device according to claim 1, wherein the control and processing unit further comprises:

a transmitter stage delivering a sine-wave electrical signal to the transmission and reception probe to ensure transmission of ultrasonic waves; and processing means having a stage amplifying the signals received by the transmission and reception probe, the stage being connected to a synchronous demodulation circuit driven by the electrical signal delivered by the transmitting stage, with the output of the synchronous demodulation circuit being connected, through a sampling circuit and a filtering stage, to a processing circuit designed to determine the frequency differences between the transmitted and received circuits.

8. The device according to claim 7, wherein the device further comprises an acoustic matching membrane mounted opposite the transmission and reception probe.

9. The device according to claim 7, wherein the device further comprises a marking system mounted at a specific distance from the transmission and reception probe to position the transmission and reception probe at exact locations on the skin of a patient.

10. A method for measuring the change in diameter of a vein by the Doppler effect, comprising:

applying the transmission and reception probe of the device according to claim 9, to the skin of a patient;

controlling operation of the transmission and reception probe in continuous mode;

moving the transmission and reception probe on the skin of the patient until an audible signal is obtained corresponding to the location of the vein sought;

holding the transmission and reception probe in a fixed position;

controlling operation of the transmission and reception probe in continuous mode in order to determine the diameter of the vein from the differences in frequency between the transmitted and received ultrasonic waves; and displaying the changes in diameter of the vein.

11. A method for measuring the change in diameter of a vein by the Doppler effect, comprising:

applying the transmission and reception probe of the device according to claim 5, to the skin of a patient;

controlling operation of the transmission and reception probe in continuous mode;

moving the transmission and reception probe on the skin of the patient until an audible signal is obtained corresponding to the location of the vein sought;

holding the transmission and reception probe in a fixed position;

controlling operation of the transmission and reception probe in discontinuous mode in order to determine the diameter of the vein from the differences in frequency between the transmitted and received ultrasonic waves; and displaying the changes in diameter of the vein.

12. The device according to claim 1, wherein the device further comprises an acoustic matching membrane mounted opposite the transmission and reception probe.

13. The device according to claim 12, wherein the compressible acoustic matching membrane has removable mounting means on the housing to allow it to be removed after use.

14. The device according to claim 13, wherein the device further comprises a marking system mounted at a specific distance from the transmission and reception probe to position the transmission and reception probe at exact locations on the skin of a patient.

15. A method for measuring the change in diameter of a vein by the Doppler effect, comprising:

applying the transmission and reception probe of the device according to claim 13, to the skin of a patient;

controlling operation of the transmission and reception probe in continuous mode;

moving the transmission and reception probe on the skin of the patient until an audible signal is obtained corresponding to the location of the vein sought;

holding the transmission and reception probe in a fixed position;

controlling operation of the transmission and reception probe in discontinuous mode in order to determine the diameter of the vein from the differences in frequency between the transmitted and received ultrasonic waves; and displaying the changes in diameter of the vein.

16. The device according to claim 12, wherein the device further comprises a marking system mounted at a specific distance from the transmission and reception probe to position the transmission and reception probe at exact locations on the skin of a patient.

17. A method for measuring the change in diameter of a vein by the Doppler effect, comprising:

applying the transmission and reception probe of the device according to claim 12, to the skin of a patient;

controlling operation of the transmission and reception probe in continuous mode;

moving the transmission and reception probe on the skin of the patient until an audible signal is obtained corresponding to the location of the vein sought;

holding the transmission and reception probe in a fixed position;

controlling operation of the transmission and reception probe in discontinuous mode in order to determine the diameter of the vein from the differences in frequency between the transmitted and received ultrasonic waves; and displaying the changes in diameter of the vein.

18. The device according to claim 1, wherein the device further comprises a marking system mounted at a specific distance from the transmission and reception probe to position the transmission and reception probe at exact locations on the skin of a patient.

19. The device according to claim 1, wherein the means of generating the first signal is an on/off button, while the means for generating the second signal is a controlled switch.

20. A method for measuring the change in diameter of a vein by the Doppler effect, comprising:

applying the transmission and reception probe of the device according to claim 1, to the skin of a patient;

controlling operation of the transmission and reception probe in continuous mode;

moving the transmission and reception probe on the skin of the patient until an audible signal is obtained corresponding to the location of the vein sought;

holding the transmission and reception probe in a fixed position;

controlling operation of the transmission and reception probe in discontinuous mode in order to determine the diameter of the vein from the differences in frequency between the transmitted and received ultrasonic waves; and displaying the changes in diameter of the vein.

* * * * *